United States Patent [19]
Wright

[11] Patent Number: 5,700,679
[45] Date of Patent: Dec. 23, 1997

US005700679A

[54] LIPID VESICLES HAVING A BILAYER CONTAINING A SURFACTANT WITH ANTI-VIRAL AND SPERMICIDAL ACTIVITY

[75] Inventor: D. Craig Wright, Gaithersburg, Md.

[73] Assignee: Novavax, Inc., Columbia, Md.

[21] Appl. No.: 661,051

[22] Filed: Jun. 7, 1996

[51] Int. Cl.$^6$ .............................. C12N 7/06; A61L 15/48
[52] U.S. Cl. .................... 435/238; 435/236; 424/450; 424/DIG. 14; 427/2.3
[58] Field of Search ........................ 435/238, 236; 424/450, DIG. 14; 427/2.3

[56] References Cited

U.S. PATENT DOCUMENTS

| | | | |
|---|---|---|---|
| 2,541,103 | 2/1951 | Sander | 514/560 |
| 4,507,281 | 3/1985 | Asculai et al. | 424/85.7 |
| 4,551,148 | 11/1985 | Riley, Jr. et al. | 424/430 |
| 5,182,104 | 1/1993 | Marcus et al. | 424/78.07 |
| 5,260,065 | 11/1993 | Mathur et al. | 424/450 |
| 5,357,636 | 10/1994 | Dresdner, Jr. et al. | 2/161.7 |
| 5,370,876 | 12/1994 | Noll et al. | 424/407 |
| 5,439,685 | 8/1995 | Augros | 424/430 |

FOREIGN PATENT DOCUMENTS

| | | |
|---|---|---|
| 0 407 257 | 1/1991 | European Pat. Off. |
| 0 461 085 | 12/1991 | European Pat. Off. |
| 3714486 | 11/1988 | Germany |
| WO 93/00114 | 1/1993 | WIPO |
| WO 94/15461 | 7/1994 | WIPO |

OTHER PUBLICATIONS

The Merck Index, Tenth Edition, Merck & Co., Inc, Rahway, NJ, p. 6522, 1983.

Buttar, H.S. et al., "Evaluation of the Cytotoxicity and Genotoxicity of the Spermicides Nonoxynol–9 and Octoxynol–9," *Toxicology Letters*, vol. 31, 65–73 (1986).

Excerpt from *The Merck Index: An Encyclopedia of Chemicals and Drugs*, 9th Edition, published by Merck and Co., Inc., Rahway, N.J., 6487 (1976).

Groves, M.J. et al., "A Note on the Interaction Between Two Phosphated Surfactants," *J. Pharm. Pharmac.*, vol. 26, 624–628 (1974).

Groves, M.J. et al., "Phase Studies of Mixed Phosphated Surfactants, n–hexane and Water," *J. Pharm. Pharmac.*, vol. 26, 616–623 (1974).

Sunamoto, J. et al., "Liposomal Membranes. XIX. Interaction Between Spermicidal Agents and Liposomes Reconstituted with Boar Spermatozoal Lipids," *Chem. Pharm. Bull.*, vol. 32, No. 8, 2891–2897 (1984).

Sunamoto, J. et al., "Liposomal Membranes. XVIII. Interaction of Spermicidal Agents with Liposomal Membranes," *Chem. Pharm. Bull.*, vol. 31, No. 12, 4230–4235 (1983).

Tryphonas, L. and Buttar, H.S., "Effects of the Spermicide Nonoxynol–9 on the Pregnant Uterus and the Conceptus of Rat," *Toxicology*, vol. 39, 177–186 (1986).

*Primary Examiner*—David M. Naff
*Assistant Examiner*—Janet M. Kerr
*Attorney, Agent, or Firm*—Lahive & Cockfield, LLP

[57] ABSTRACT

A novel formulation having anti-viral and spermicidal properties has been developed. The formulation contains lipid vesicles having an outer bilayer formed of a non-ionic amphiphile, a surfactant such as having spermicidal and/or anti-viral activity, an oil and a sterol. The selection of the components making the vesicle is such that the formulation provides rapid spermicidal or anti-viral activity. The formulation and methods of the invention are particularly useful in the mucous membranes such as the vaginal tract and has been tested against viruses such as HIV and Vaccinia.

61 Claims, No Drawings

5,700,679

LIPID VESICLES HAVING A BILAYER CONTAINING A SURFACTANT WITH ANTI-VIRAL AND SPERMICIDAL ACTIVITY

BACKGROUND OF THE INVENTION

The present invention relates to methods of constructing non-phospholipid-based liposomes (Novasome®) containing surfactants which are latex compatible and inactivate enveloped viruses and spermatozoa on contact. Formulations useful for coating on condoms or for vaginal insertion are also disclosed. NONOXYNOL-9 is the preferred surfactant for use in the formulation and methods.

The portal of entry of pathogenic viruses in humans are predominantly the mucus membranes and the respiratory tract. The first step in any infection is attachment or colonization with subsequent invasion and dissemination of the infectious pathogen. Inactivation of potential pathogens at the site of colonization could prevent many infectious diseases. The present inventions were designed to inactivate spermatozoa and enveloped viruses on contact.

Although there has been some experimentation using liposomes as a delivery system for a variety of materials, no successful use of liposomes or other lipid vesicles as a contact anti-viral agent or contact spermicide has been reported. The major problems are compatibility and stability, particularly since the environments for use are often perfect "laboratories" for growing bacteria which could attach and degrade the preparations. The formulations must be able to operate over a physiologically broad spectrum of pH and at physiological temperatures. The pH and temperature requirements have made use of many phospholipid formulations, or classic liposomes, inappropriate because of their instability. Further, many formulations using either phospholipids or non-phospholipids are not latex compatible, a requirement if the formulation is to be used in connection with condoms, or are irritating to the mucous membranes at the delivery site. Both of these properties, latex compatibility and lack of irritation, are important for a successful product.

In the last few years, several companies, primarily IGI, Inc., through its former subsidiaries Micro Vesicular Systems, Inc. and NovaVax, Inc., and L'Oreal, have developed and popularized non-phospholipid lipid vesicles and their uses. U.S. Pat. No. 4,911,928, U.S. Pat. No. 4,895,452, U.S. Pat. No. 5,260,065, and United States Patent application Ser. No. 08/482,552, the disclosures of which are incorporated herein by reference, disclose various formulations and methods for making lipid vesicles which utilize a variety of non-phospholipid materials. These patents and this application, together with variations on the methods and materials disclosed therein, have been used to develop a variety of products ranging from vaccines to skin care products. However, to date, no formulations have been made which successfully meet all the requirements necessary for a spermicidal or anti-viral product which is latex compatible and stable.

Accordingly, an object of the present invention is to provide a virus-inactivating lipid vesicle which inactivates viruses on contact.

A further object of the invention to provide non-irritating, stable preparations that inactivate viruses, especially enveloped viruses, on skin or mucous membranes.

Another further object of the present invention is to provide a method of preventing a viral infection in an affected subject by administrating a virus-inactivating lipid vesicle to the subject.

A still further object of the present invention is to provide a method of inactivating spermatozoa by contacting the spermatozoa with a spermicidal lipid vesicle.

These and other objects and features of the invention will be apparent from the Description of the Preferred Embodiments and the Claims.

SUMMARY OF THE INVENTION

The present invention features methods of inactivating spermatozoa and enveloped viruses such as HIV and vaccinia viruses, on contact, as well as a formulation having these properties. The invention is based, at least in part, on the discovery that a lipid vesicle formulation could be made having a sufficient portion of the anti-viral or spermaticidal surfactant carried in the lipid bilayers such that the formulation was active without vesicle breakdown. This formulation may also be less irritating than other formulations.

The formulation useful in the present invention contains lipid vesicles consisting of a non-ionic amphiphile, an oil, a sterol and a surfactant having anti-enveloped viral or spermicidal activity. The preferred surfactant is a nonoxyphenol surfactant, most preferably NONOXYNOL-9. The non-ionic amphiphile, the oil and the surfactant are selected such that at least a portion of the surfactant is carried in the outer bilayers of the lipid vesicle.

Preferred non-ionic amphiphiles are selected from the group consisting of Polyoxyethylene (POE). ethers of fatty alcohols, POE esters of fatty acids, glycerol mono- and dilaurate, glycerol mono- and distearate, and POE sorbitan fatty acid ethers, with glycerol monostearate being most preferred. The oil should be one in which the surfactant has a low solubility, preferably an oil in which the surfactant is not dissolvable. If NONOXYNOL-9 is used as the surfactant, vegetable oils such as soybean oil are preferred, while mineral oils are not usable. It is theorized that if the surfactant is dissolvable in the oil, it is not in the lipid bilayers, but if it is not dissolvable, it must be carried at the bilayer surface.

While almost any sterol can be used, cholesterol or phytosterols such as soy sterol are preferred. The vesicles may also contain a charge producing agent, preferably a negative charge producing agent such as oleic acid. The vesicles may be formulated for delivery using a pharmaceutically acceptable carrier such as saline. The vesicles can be formulated into a cream, e.g., a cream suitable for vaginal insertion, or it may be adapted for use on or with a condom.

The methods of the invention use this formulation for its anti-enveloped viral activity or spermicidal activity. While some of the formulations of the invention have both anti-enveloped viral and spermicidal activity, e.g., formulations using NONOXYNOL-9 (poly(ethylene glycol) p-nonylphenyl ether; nonylphenoxypolyethoxyethanol, average number of ethylene oxide units per molecule is indicated by number following nonoxynol (e.g. nonoxynol-9 for n=9)) as the surfactant, it is also possible to use other surfactants which have only one of these properties. Some of the other surfactants which may be used include the TRITON-X (polyethylene glycol p-isooctylphenyl ether) family of surfactants which have been shown to have some spermicidal properties, or cetyl pyridinium chloride which has been shown to have some anti-viral properties. Briefly, the methods of the invention expose the spermatozoa or enveloped virus to the formulation and allow the formulation to act on the spermatozoa or virus. Since the formulations of the invention provide rapid activity, exposure can be very short, possibly on the order of seconds. For sexually

3 transmitted viruses and spermatozoa, the formulations can be made into vaginal creams or condom lubricants. For other viruses, other forms, such as nasal sprays, could be used.

The following description and the claims will further clarify the scope of the invention.

DESCRIPTION OF THE PREFERRED EMBODIMENTS

The present invention provides methods of inactivating enveloped viruses and spermatozoa, as well as a formulation useful in those methods. The invention uses lipid vesicles which include a spermicidal or anti-viral surfactant in the outer bilayers to provide rapid activity without the necessity of vesicle breakdown.

The basic vesicle of the invention is formed of a non-ionic amphiphile such as glycerol monostearate, a sterol such as soy phytosterol, a surfactant showing the anti-viral or spermicidal (or both) activities such as NONOXYNOL-9, and an oil such as soybean oil. The oil, non-ionic surfactant and surfactant are selected such that at least a portion of the surfactant is in the outer bilayers of the vesicle so it can provide the requisite activity without breakdown of the vesicles. This requires compatibility between the non-ionic amphiphile and the surfactant, and it further requires that the surfactant is not dissolvable in the oil. Selection of any surfactant requires the ability to be used in stable lipid vesicles as well as compatibility testing, all of which are standard in the art. For example, if the formulations are going to be used with latex; e.g., with latex condoms, they must be latex-compatible, which can be determined rapidly using standard latex-compatibility testing. One means of selecting the proper mix of materials is a screening assay using spermicidal activity; the lipid vesicles must be able to inactivate spermatozoa in less than 20 seconds. If none of the surfactant was in the outer bilayers, rapid spermicidal activity could not occur with immediate lysis of the lipid vesicles, which is not found. Tests for spermicidal activity and anti-viral activity are described in the Examples.

The invention is more clearly understood through the following, non-limiting Examples.

EXAMPLE 1

Preparation of GNP9SO Novasomes® Containing Nonoxynol-9

Table 1 contains the materials utilized to produce GNP9SO Novasomes® containing NONOXYNOL-9 as the surfactant, glycerol monostearate as the amphiphile, soybean oil, and oleic acid as the negative charge producing agent.

TABLE 1

| Chemical Component | Weight |
| --- | --- |
| Glycerol monostearate | 13.7 grams |
| Soya sterol (or cholesterol) | 3.8 grams |
| NONOXYNOL-9 | 7.2 grams |
| Soybean oil | 16 grams |
| Oleic acid | 250 microliters |

The components shown in Table 1 form the lipid-oil phase which is heated for 1 hour at 86° C. to achieve uniformity. Water is heated to 65° C. The GNP9SO Novasomes® are then produced by injecting the water phase into the lipid phase on a volume/volume basis of 13 parts lipid-oil to 37 parts water. GNP9SO Novasomes® can be produced manually, with reciprocating syringe instrumentation or continuous flow instrumentation.

EXAMPLE 2

Characterization of NONOXYNOL-9 Novasome® Preparations

After production of Novasomes®, characterization studies are performed. All preparations are tested for sterility and pH. Preparations are also sized on a Coulter LS 230 Laser sizing instrument equipped with a circulating waterbath. Table 2 shows the physical characteristics of the vesicles. Tables 3 and 4 show tests for anti-viral activity in vitro utilizing cell lines which allow viral proliferation. Tables 5 and 6 show latex compatibility, Table 7 shows anti-spermicidal activity using the Sander-Cramer assay, and Table 8 shows oral toxicity data.

TABLE 2

| Chemical Components | Charge | pH | Mean Coulter Size in µm | Mean Coulter Range in µm |
| --- | --- | --- | --- | --- |
| GNP9SO Novasomes ® | Negative | 4.52 | 0.598 | 0.375–0.839 |

EXAMPLE 3

Anti-Viral Assays

A. HIV-1 MN Viricidal Assay

The Novasome® preparation of Example 1 was tested for anti-viral activity against HIV-1. 100 microliters of HIV-1 Mn 1000× pelleted virus Lot #50-013 (TC ID$_{50}$/ml =$10^{-6}$) was mixed for 30 minutes with either 100 microliters of water for injection or 100 microliters of Novasome® preparations. 1.8 mL of tissue culture medium was then added to each preparation. Serial 10 fold dilutions were then performed from $10^{-2}$ to $10^{-6}$. 0.4 mL of each dilution was then placed in tubes containing C8166 cells, a HTLV-1 transformed T cell line. These combined materials were then incubated at 37° C. for 2 hours, washed 3 times in phosphate buffered saline, resuspended in fresh medium and each dilution plated in four replicate wells. Cells were fed twice weekly. Cells were observed at 7 and 14 days for cytopathic effects and supernatants were collected for p24 assay determinations as confirmation of viral proliferation. Tissue Culture Infective Dose (TC ID$_{50}$) (the amount of virus required to infect 50% of a tissue culture) calculations were performed based on the results of the p24 determinations.

The results are illustrated in Table 3. The Novasome® preparation clearly has anti-HIV activity.

TABLE 3

| Test article | TC ID$_{50}$ at 1 week | TC ID$_{50}$ at 2 weeks |
| --- | --- | --- |
| Water | $10^{-4.75}$ | $10^{-4.75}$ |
| GNP9SO Novasomes ® | 0 | 0 |

B. Vaccinia WR Viricidal Assay

The Novasome® preparation of Example 1 was also tested for anti-viral activity against Vaccinia WR. 100 microliters of Vaccinia WR 1000× pelleted virus Lot #68-016 (TCID-50/ml=$10^{-9}$) was mixed for 30 minutes with either 100 microliters of water for injection or 100 microliters of the Novasome® preparation. 200 µL of tissue culture medium was then added to the preparations. Serial 10 fold dilutions were then performed on the virus and no virus controls from $10^{-1}$ to $10^{-6}$. 40 μL of each dilution was then placed in 96 well tissue culture plates containing BSC-1 cells. There were five replicates at each dilution, and duplicate plates were prepared. These combined materials were then incubated at 37° C. for 2 hours, washed 1 time in phosphate buffered saline, resuspended in fresh medium. Cells were observed at 3 and 7 days for cytopathic effects. (3-(4,5-dimethylthiazol-2-yl)-5-(3-carboxymethoxyphenyl) -2-(4-sulfophenyl)-2H-tetrazolium, inner salt; also known as Owen's reagent) (MTS) was run on the first plate at 3 days; the second plate was refed at three days and the MTS was run on this plate at 7 days.

Table 4 shows the results of the Vaccinia WR assay. Again, it is clear that the Novasome® preparation has anti-viral activity.

TABLE 4

| Test article | TC ID$_{50}$ at 3 days | TC ID$_{50}$ at 7 days |
|---|---|---|
| Water | $10^{-7}$ | $10^{-7}$ |
| GNP9SO Novasomes ® | 0 | 0 |

EXAMPLE 4

Latex Compatibility Testing

The Novasome® preparation of Example 1 was also tested for latex compatibility. Three types of condoms, Trojan-Enz Non-Lubricated LO316RP, Lifestyles 0602258800, and Aladan were tested in this assay. The Novasome® preparation was applied to 13 condoms of each brand in 5 seconds using a soft brush and placed on a cheesecloth. Condoms were then conditioned in a humidity chamber at 90% relative humidity (RH) @38° C. for 30 minutes. They were then washed, dried, and tested for elongation and tensile strength. Another 13 condoms of each brand were treated as above but after conditioning were mounted directly onto the Airburst test fixture and tested. 80 condoms of each brand without the Novasome® preparation were tested for these properties as controls. Table 5 shows the results of the latex compatibility testing without the Novasome® preparation while Table 6 shows the testing with the Novasome® preparation. It is clear that the Novasome® preparation does not effect the properties of the latex condoms in short time compatibility testing.

TABLE 5

| Condom Brand | Trojan Enz Non-Lubricated | Lifestyle | Aladan |
|---|---|---|---|
| Elongation % | 783 | 827 | 802 |
| Tensile Strength, MPa | 25.9 | 29.8 | 29.0 |
| Pressure kPa | 2.3 | 1.3 | 2.2 |
| Volume, Liters | 39.4 | 40.7 | 36.5 |

TABLE 6

| Condom Brand | Trojan Enz Non-Lubricated | Lifestyle | Aladan |
|---|---|---|---|
| Elongation % | 777 | 841 | 848 |
| Tensile Strength, MPa | 26.8 | 29.1 | 30.2 |

TABLE 6-continued

| Condom Brand | Trojan Enz Non-Lubricated | Lifestyle | Aladan |
|---|---|---|---|
| Pressure kPa | 2.1 | 1.2 | 1.9 |
| Volume, Liters | 39.4 | 40.7 | 36.5 |

EXAMPLE 5

Sander-Cramer Spermicidal Assay

In this Example, the preparation of Example 1 was tested for spermicidal activity using the Sander-Cramer spermicidal assay. A series of dilutions of the test compound are prepared using 0.9% saline. 1 mL of test article is mixed with 0.2 mL of human semen in a 13×100 min. test tube by drawing the mixture into a pipet and forcibly expressing the mixture. This procedure is repeated 6 times. A hanging drop of the mixture is prepared and five fields are observed under low power magnification. The whole process from mixing to microscopic observation must be accomplished in less than 20 seconds. The end point is the highest dilution that immobilizes spermatozoa in less than 20 seconds.

Table 7 shows the results of the Sander-Cramer assay. The vesicles of the invention not only allowed a higher NP-9 concentration than standard DMSO preparations, it also killed the sperm at a higher dilution, showing greater activity.

TABLE 7

| Test article | Highest Spermicidal NP9 Dilution | Concentration |
|---|---|---|
| GNP9SO Novasomes ™ | 528 | 32.5 mg/mL |
| NP9 Control | 91 | 10 mg/mL in DMSO |

EXAMPLE 6

Rat Oral Toxicity Study

In this Example, the preparation of Example 1 was tested for oral toxicity. One group of Sprague-Dawley rats consisting of five males and five females were fasted overnight. The following morning after weighing each rat received three milliliters by gavage of the GNP9SO Novasome® preparation, the maximum allowable oral dose for rats. Animals were observed daily for sickness and mortality and individual body weights were obtained on day 7 and 14. The results are reported in Table 8.

TABLE 8

| Rats | Mean Total Weight Gain Day 0–14 |
|---|---|
| Male | 126.66 g |
| Female | 24.13 g |

Based on the results of the studies shown in the Examples, it is clear that the preparations of the invention show spermicidal and anti-viral activity while being latex compatible and safe orally. These preparations are particularly useful for spermicidal and viricidal vaginal creams.

The forgoing formulations and Examples are merely illustrative and the scope of the invention is governed by the following claims.

What is claimed is:

1. A method of inactivating spermatozoa comprising the step of exposing said spermatozoa to a latex-compatible lipid vesicle formulation having topical spermicidal activity; said lipid vesicle formulation containing lipid vesicles having an outer bilayer wherein, said lipid vesicles include a non-ionic amphiphile, an oil, a sterol, and a spermicidal surfactant, wherein said lipid vesicles are formed primarily of said non-ionic amphiphile, wherein said non-ionic amphiphile, said oil and said spermicidal surfactant are selected such that said spermicidal surfactant is not dissolvable in said oil and at least a portion of said spermicidal surfactant is in the outer bilayer of said lipid vesicle.

2. The method of claim 1 wherein said spermicidal surfactant has an average number of nine ethylene oxide units per molecule.

3. The method of claim 1 wherein said non-ionic amphiphile is selected from the group consisting of POE ethers of fatty alcohols, POE esters of fatty acids, glycerol monolaurate, glycerol dilaurate, glycerol monostearate and glycerol distearate, and POE sorbitan fatty acid ethers.

4. The method of claim 1 wherein said non-ionic amphiphile comprises glycerol monostearate.

5. The method of claim 1 wherein said sterol is selected from the group consisting of cholesterol and phytosterols.

6. The method of claim 5 wherein said sterol comprises soy sterol.

7. The method of claim 1 wherein said oil comprises a vegetable oil.

8. The method of claim 7 wherein said vegetable oil comprises soybean oil.

9. The method of claim 1 wherein said lipid vesicle further comprises a charge producing agent.

10. The method of claim 9 wherein said charge producing agent comprises a negative charge producing agent.

11. The method of claim 10 wherein said negative charge producing agent comprises oleic acid.

12. The method of claim 1 wherein said formulation further comprises a pharmaceutically acceptable carrier.

13. The method of claim 12 wherein said formulation is in the form of a cream.

14. The method of claim 13 wherein said formulation is used for vaginal insertion.

15. The method of claim 1 wherein said formulation is coated on a condom.

16. A method of inactivating an enveloped virus comprising the step of exposing said enveloped virus to a latex-compatible lipid vesicle formulation, said lipid vesicle formulation containing lipid vesicles having an outer bilayer wherein, said lipid vesicles include a non-ionic amphiphile, an oil, a sterol, and a nonoxyphenol surfactant, wherein said lipid vesicles are formed primarily of said non-ionic amphiphile, wherein said non-ionic amphiphile, said oil and said nonoxyphenol surfactant are selected such that said nonoxyphenol surfactant is not dissolvable in said oil and at least a portion of said nonoxyphenol surfactant is in the outer bilayer of said lipid vesicle.

17. The method of claim 16 wherein said nonoxyphenol surfactant has an average number of nine ethylene oxide units per molecule.

18. The method of claim 16 wherein said non-ionic amphiphile is selected from the group consisting of POE ethers of fatty alcohols, POE esters of fatty acids, glycerol monolaurate, glycerol dilaurate, glycerol monostearate and glycerol distearate, and POE sorbitan fatty acid ethers.

19. The method of claim 18 wherein said non-ionic amphiphile comprises glycerol monostearate.

20. The method of claim 16 wherein said sterol is selected from the group consisting of cholesterol and phytosterols.

21. The method of claim 20 wherein said sterol comprises soy sterol.

22. The method of claim 16 wherein said oil comprises a vegetable oil.

23. The method of claim 22 wherein said vegetable oil comprises soybean oil.

24. The method of claim 16 wherein said lipid vesicle further comprises a charge producing agent.

25. The method of claim 24 wherein said charge producing agent comprises a negative charge producing agent.

26. The method of claim 25 wherein said negative charge producing agent comprises oleic acid.

27. The method of claim 16 wherein said formulation further comprises a pharmaceutically acceptable carrier.

28. The method of claim 27 wherein said formulation is in the form of a cream.

29. The method of claim 28 wherein said formulation is used for vaginal insertion.

30. The method of claim 16 wherein said formulation is coated on a condom.

31. A method of inactivating spermatozoa comprising the step of exposing said spermatozoa to a latex-compatible lipid vesicle formulation, said lipid vesicle formulation containing lipid vesicles having an outer bilayer, wherein said lipid vesicles include a non-ionic amphiphile, an oil, a sterol, and a nonoxyphenol surfactant, wherein said lipid vesicles are formed primarily of said non-ionic amphiphile, wherein said non-ionic amphiphile, said oil and said nonoxyphenol surfactant are selected such that said nonoxyphenol surfactant is not dissolvable in said oil and at least a portion of said nonoxyphenol surfactant is in the outer bilayer of said lipid vesicle.

32. The method of claim 31 wherein said nonoxyphenol surfactant has an average number of nine ethylene oxide units per molecule.

33. The method of claim 31 wherein said non-ionic amphiphile is selected from the group consisting of POE ethers of fatty alcohols, POE esters of fatty acids, glycerol monolaurate, glycerol dilaurate, glycerol monostearate and glycerol distearate, and POE sorbitan fatty acid ethers.

34. The method of claim 33 wherein said non-ionic amphiphile comprises glycerol monostearate.

35. The method of claim 31 wherein said sterol is selected from the group consisting of cholesterol and phytosterols.

36. The method of claim 35 wherein said sterol comprises soy sterol.

37. The method of claim 31 wherein said oil comprises a vegetable oil.

38. The method of claim 37 wherein said vegetable oil comprises soybean oil.

39. The method of claim 31 wherein said lipid vesicle further comprises a charge producing agent.

40. The method of claim 39 wherein said charge producing agent comprises a negative charge producing agent.

41. The method of claim 40 wherein said negative charge producing agent comprises oleic acid.

42. The method of claim 31 wherein said formulation further comprises a pharmaceutically acceptable carrier.

43. The method of claim 42 wherein said formulation is in the form of a cream.

44. The method of claim 43 wherein said formulation is used for vaginal insertion.

45. The method of claim 31 wherein said formulation is coated on a condom.

46. A formulation for inactivating spermatozoa or enveloped viruses comprising a latex-compatible lipid vesicle formulation, wherein said lipid vesicle formulation includes lipid vesicles, wherein said vesicles include a non-ionic amphiphile, an oil, a sterol, and a nonoxyphenol surfactant, wherein said lipid vesicles are formed primarily of said non-ionic amphiphile, wherein said non-ionic amphiphile, said oil and said nonoxyphenol surfactant are selected such that said nonoxyphenol surfactant is not dissolvable in said oil and at least a portion of said nonoxyphenol surfactant is in the outer bilayer of said lipid vesicle.

47. The formulation of claim 46 wherein said nonoxyphenol surfactant has an average number of nine ethylene oxide units per molecule.

48. The formulation of claim 46 wherein said non-ionic amphiphile is selected from the group consisting of POE ethers of fatty alcohols, POE esters of fatty acids, glycerol monolaurate, glycerol dilaurate, glycerol monostearate and glycerol distearate, and POE sorbitan fatty acid ethers.

49. The formulation of claim 48 wherein said non-ionic amphiphile comprises glycerol monostearate.

50. The formulation of claim 46 wherein said sterol is selected from the group consisting of cholesterol and phytosterols.

51. The formulation of claim 50 wherein said sterol comprises soy sterol.

52. The formulation of claim 46 wherein said oil comprises a vegetable oil.

53. The formulation of claim 52 wherein said vegetable oil comprises soybean oil.

54. The formulation of claim 46 wherein said lipid vesicles further comprises a charge producing agent.

55. The formulation of claim 54 whereto said charge producing agent comprises a negative charge producing agent.

56. The formulation of claim 55 wherein said negative charge producing agent comprises oleic acid.

57. The formulation of claim 46 wherein said formulation further comprises a pharmaceutically acceptable carrier.

58. The formulation of claim 57 wherein said formulation is in the form of a cream.

59. The formulation of claim 58 wherein said formulation is suitable for vaginal insertion.

60. The formulation of claim 46 wherein said formulation is suitable for coating on a condom.

61. A condom having a coating with spermicide or enveloped virus inactivating activity, said condom having the formulation of claim 46.

* * * * *